United States Patent [19]

Geering

[11] 4,397,859

[45] Aug. 9, 1983

[54] INSECTICIDE

[75] Inventor: Quinton A. Geering, Cambridge, England

[73] Assignee: Fisons Limited, England

[21] Appl. No.: 261,134

[22] Filed: May 4, 1981

Related U.S. Application Data

[63] Continuation of Ser. No. 3,944, Jan. 16, 1979, abandoned, which is a continuation of Ser. No. 727,868, Sep. 29, 1976, abandoned, which is a continuation of Ser. No. 552,144, Feb. 24, 1975, abandoned, which is a continuation of Ser. No. 335,425, Feb. 23, 1973, abandoned.

[30] Foreign Application Priority Data

Feb. 25, 1972 [GB] United Kingdom ................ 8723/72

[51] Int. Cl.$^3$ ...................... A01N 43/76; A01N 43/80

[52] U.S. Cl. .................................. 424/272; 424/47; 424/357

[58] Field of Search ......................................... 424/272

[56]  References Cited

U.S. PATENT DOCUMENTS

| | | | |
|---|---|---|---|
| 2,431,844 | 12/1947 | Synerholm | 424/282 X |
| 2,856,411 | 10/1958 | Prill | 424/282 X |
| 2,951,850 | 9/1960 | Hartle et al. | 424/282 X |
| 3,736,338 | 5/1973 | Gates et al. | 424/282 X |

*Primary Examiner*—Dale R. Ore
*Attorney, Agent, or Firm*—Wenderoth, Lind & Ponack

[57] ABSTRACT

An insecticidal composition particularly valuable for use indoors, e.g. against cockroaches, comprises:
- (A) 2,2-dimethyl-1,3-benzodioxol-4-yl H-methylcarbamate; and
- (b) pyrethrin.

8 Claims, No Drawings

INSECTICIDE

This is a Continuation of Ser. No. 3,944, filed Jan. 16, 1979, which is a Continuation of Ser. No. 727,868, filed Sept. 29, 1976, which is a Continuation of Ser. No. 552,144, filed Feb. 24, 1975, which is a Continuation of Ser. No. 335,425 filed Feb. 23, 1973, all abandoned.

The present invention relates to insecticidal compositions, their preparation and their use.

The invention provides an insecticidal composition comprising:
  (A) 2,2-dimethyl-1,3-benzodioxol-4-yl N-methylcarbamate; and
  (B) pyrethrin.

In addition, the invention provides a method of combating insects at a locus infested or liable to be infested with them, which method comprises applying to the locas an insect-combating amount of the composition.

The essential components (A) and (B) are known as insecticides, but the present mixtures are unexpectedly advantageous. The mixtures are synergistic, being surprisingly effective. They are particularly useful against domestic insect pests, especially cockroaches. The present composition achieves a more rapid killing of the insects, e.g. after an hour, than the additive effect of the essential components.

The proportions of (A) to (B) can vary over a wide range depending on such factors as the particular ingredients employed, the particular locus to be treated, the particular pests to be combated and the particular effect desired (e.g. whether a long residual period of control is required). Overall, however, the proportions of (A) to (B) may be for example from 1:50 to 40:1, usually from 1:10 to 10:1. Proportions from 1:5 to 5:1, e.g. from 1:2 to 2:1, a specific suitable proportion being 1:1, may especially be employed, e.g. where a concentrate containing no additional material as synergist for the pyrethrin is diluted at the point of use against domestic insect pests and applied by spraying to give long residual control. Parts, proportions and percentages in this specification are by weight unless otherwise indicated.

Component (B) may be a natural or synthetic pyrethrin, e.g:
  Pyrethrin I (the pyrethrolone ester of chrysanthemic acid),
  Cinerin I (the cinerolone ester of chrysanthemic acid),
  Pyrethrin II (the pyrethrolone ester of pyrethric acid),
  Cinerin II (the cinerolone ester of pyrethric acid),
  Jasmolin I (the jasmololone ester of chrysanthemic acid),
  Jasmolin II (the Jasmololone ester of pyrethric acid),
  Allethrin (2-allyl-4-hydroxy-3-methyl-2-cyclopenten-1-one ester of 2,2-dimethyl-3-(2-methylpropenyl)-cyclopropanecarboxylic acid),
  Barthrin (6-chloropiperonyl 2,2-dimethyl-3-(2-methylpropenyl)cyclopropane carboxylate),
  Dimethrin (2,4-dimethylbenzyl 2,2-dimethyl-3-(2-methylpropenyl)cyclopropane carboxylate),
  Tetramethrin (1-cyclohexene-1,2-dicarboximidomethyl 2,2-dimethyl-3-(2-methylpropenyl)-cyclopropane carboxylate),
  Resmethrin (5-benzyl-3-furylmethyl-cis, trans-chrysanthemate) or
  Bioresmethrin (5-benzyl-3-furylmethyl-trans-chrysanthemate).

Component (B) may be a mixture of pyrethrins. Preferably (B) is naturel pyrethrin or a mixture of natural and synthetic pyrethrins.

The compositions can be prepared by admixing the ingredients. The compositions may be initially produced in the form of concentrates, e.g. containing 0.5–85% in toto of the essential components (A) and (B), and these may be diluted with water or a hydrocarbon at the point of use for application by spraying, generally such that the concentration in toto of (A) and (B) is 0.02–3%, e.g. 0.1–3%, preferably 0.15–2%. In one embodiment, there is applied an aqueous spray containing ¼–1%, e.g. ½%, of component (A).

Alternatively, the compositions can be produced directly for application, e.g. in the form of dusts or granules. A composition of particular interest is an aerosol composition. Hence, aerosol packs containing such a composition under pressure can be produced.

As illustrations of the concentrations which may be used in compositions applied to combat domestic insect pests: in a spray applied for residual effect on surfaces, a content of 0.002–0.5% (B) and 0.025–0.5% (A) may be employed. For aerosol application for residual effect on surfaces, a content of 0.002–0.5% (B) and 0.1–5% (A) may be employed. For aerosol application for the treatment of air spaces, a content of 0.002–0.5% (B) and 0.001–0.1% (A) may be employed.

Thus, overall the present compositions may contain for example 0.003–85% in toto of (A) and (B).

The compositions may contain an additional material which is a synergist for (B). Such an additional material can be for example piperonyl butoxide (5-(2-(2-butoxyethoxy)ethoxymethyl)-6-propyl-1,3-benzodioxole), piprotal (bis-(2-(2-butoxyethoxy)ethyl) acetal), sesamin (2,6-bis-(3,4-methylenedioxyphenyl)-3,7-dioxabicyclo(3,3,0)-octane) or sesamex (2-(3,4-methylenedioxyphenoxy) ethyl-3,6,9-trioxaundecane). The effect of such additional material varies with the particular component (B) employed. The amount of such additional material may be for example 2–20 parts per part of (B).

The compositions normally contain a carrier and/or a surface active agent.

The carrier may be a liquid, e.g. water (e.g. water used to dilute a concentrate for application). An organic solvent may be present with the water though this is not usually employed.

The carrier may be a liquid other than water, for example an organic solvent, e.g. a water-immiscible solvent, for instance a hydrocarbon which boils within the range 130°–270° C., in which the essential components are dissolved or suspended. A concentrate containing an organic solvent may contain a surface active agent so that the concentrate acts as a self-emulsifiable concentrate on admixture with water.

The carrier may be a solid, which may be finely divided. Examples of suitable solids are clays, sand, mica, chalk, attapulgite, diatomite, perlite and sepiolite, and synthetic solid carriers, e.g. silicas, silicates and lignosulphonates.

Wettable powders soluble or dispersible in water may be formed by admixing the essential components with or without a carrier with a surface active agent, or the essential components may be admixed with a solid carrier to form a dust, powder or granular product.

The term 'surface active agent' is used in the broad sense to include materials variously called emulsifying agents, dispersing agents and wetting agents. Such agents are well known in the insecticide art.

The surface active agents used may comprise anionic surface active agents, for example soaps, fatty sulphate esters such as dodecyl sodium sulphate, octadecyl sodium sulphate and cetyl sodium sulphate, fatty aromatic sulphonates such as alkyl-benzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise non-ionic agents, for example condensation products of fatty acids, fatty alcohols or fatty substituted phenols with ethylene oxide, or fatty esters and ethers of sugars or polyhydric alcohols, or the products obtained from the latter by condensation with ethylene oxide, or the products known as block copolymers of ethylene oxide and propylene oxide.

The surface active agents may also comprise cationic agents, for example cetyl trimethylammonium bromide.

Preferred surface active agents include fatty alkyl sulphates, alkyl aryl sulphonates, fatty alkyl ethoxylates, sulphated fatty alkyl ethoxylates, dialkyl sulphosuccinate esters, the amide condensation product of oleic acid and N-methyl taurine, lignin condensation product of oleic acid and N-methyl taurine, lignin sulphonate salts, sulphonated naphthalene-formaldehyde condensates and sulphonated urea-formaldehyde condensates.

The compositions can contain a coating of a sticker, e.g a vinyl resin or casein, and this can prolong the residual activity.

The compositions may be in the form of an aerosol composition, suitably containing a solvent, besides the propellant, which is suitably a polyhalogenated alkane such as dichlorodifluoromethane.

The compositions can contain besides (A) and (B) other pesticides, particularly another insecticide. Particular advantages are obtained where the other insecticide is DDVP (2,2-dichlorovinyl dimethyl phosphate). The other insecticide, e.g. DDVP, may be present for example in such amount that the proportion of (A) to it is from 1:50 to 20:1, e.g. from 1:20 to 10:1.

The present composition is active against a wide range of insect pests. Particularly, however, it is applied indoors, e.g. in buildings (for instance public buildings, houses, flats and warehouses) or on ships, e.g. in food preparation or storage areas. It is particularly useful against domestic insect pests such as ants, bed bugs, fleas, houseflies, silverfish, mosquitoes, wasps, carpet beetles and crickets, and especially against cockroaches.

When used indoors, the compositions are usually employed at a rate of 10–1000, e.g. 50–1000 but preferably 10–500, mg of component (A) per square meter. When used to combat insects on plants, the soil, land or aquatic areas a rate of ¼–2, e.g. ½–2, kg of (A) per hectare may be used.

The essential components may be mixed immediately before use. Desirably, however, they would already have been mixed.

The invention is illustrated by the following Examples.

EXAMPLE 1

A wettable powder was made up by admixing and grinding the following ingredients:

| | |
|---|---|
| 2,2-Dimethyl-1,3-benzodioxol-4-yl N—methylcarbamate | 25% |

-continued

| | |
|---|---|
| Pyrethrin 1 | 25% |
| Fine precipitated silica | 42.5% |
| Sodium oleoyl N—methyl tauride | 2.5% |
| Calcium lignin sulphenate | 5% |
| | 100% |

EXAMPLE 2

The wettable powder prepared as in Example 1 was admixed with water to form a spray liquid containing 0.375% of the N-methylcarbamate and sprayed at a rate equivalent to 50 mg of total active ingredient per square meter onto an area of one square meter which was then infested with 100 cockroaches.

Comparative sprayings at 25 mg of active ingredient per square meter were carried out on similar areas with sprays made up from analogous wettable powders containing as active ingredient 25% of the N-methylcarbamate alone or of the pyrethrin alone.

After 1 hour, the composition according to the invention had killed all the cockroaches, while the two comparative compositions had still left a large proportion of cockroaches alive, and the composition containing only the N-methylcarbamate had not killed all the cockroaches until several hours later.

EXAMPLE 3

An 80% wettable powder formulation of 2,2-dimethyl-1,3-benzodioxol-4-yl N-methylcarbamate was admixed with water to form a spray liquid containing 0.5% of the active ingredient. To this was added a commercial emulsifiable concentrate containing 5% natural pyrethrins and 50% piperonyl butoxide at a rate of 2 oz (57 g) of concentrate per Imperial gallon (4.5 liters).

EXAMPLE 4

The composition of Example 3 was sprayed on board ship to combat cockroaches using equipment and procedures usual for this purpose. Rapid kill of the cockroaches was obtained and a high level of control achieved for a long period.

I claim:

1. A synergistic insecticidal composition consisting essentially of:
   (A) 2,2-dimethyl-1,3-benzodioxol-4-yl N-methylcarbamate, and
   (B) a pyrethrin selected from the group consisting of natural pyrethrin, resmethrin, tetramethrin and bioresmethrin, said natural pyrethrin comprising a mixture of pyrethrins I and II, cinerins I and II and jasmolins I and II; wherein the proportion of (A) to (B) is from 10:1 to 1:1 by weight.

2. The composition according to claim 1, wherein (B) is natural pyrethrin.

3. The composition according to claim 1 which contains 2,2-dichlorovinyl dimethyl phosphate.

4. The composition according to claim 3, wherein the proportion of (A) to 2,2-dichlorovinyl dimethyl phosphate is from 1:50 to 20:1 by weight.

5. The composition according to claim 1 which additionally contains piperonyl butoxide as a synergist for (B).

6. A method of combatting insects at a locus to be protected from them, which method comprises applying to the locus an insecticidally effective amount of a synergistic insecticidal composition consisting essentially of:
- (A) 2,2-dimethyl-1,3-benzodioxol-4-yl N-methylcarbamate, and
- (B) a pyrethrin selected from the group consisting of natural pyrethrin, resmethrin, tetramethrin and bioresmethrin, said natural pyrethrin comprising a mixture of pyrethrin I and II, cinerins I and II and jasmolins I and II; wherein the proportion of (A) to (B) is from 10:1 to 1:1 by weight.

7. The method according to claim 6, wherein the composition is applied indoors.

8. The method according to claim 7, wherein the composition is applied in the amount of 10–1,000 mg of component (A) per square meter.

* * * * *